(12) United States Patent
Kojima et al.

(10) Patent No.: US 8,318,811 B2
(45) Date of Patent: *Nov. 27, 2012

(54) METHOD FOR TREATING AN INFLAMMATORY BOWEL DISEASE USING 2-AMINO-2-[4-(3-BENZYLOXYPHENYL-THIO)-2-CHLOROPHENYL]ETHYL-1,3-PROPANEDIOL OR A SALT THEREOF

(75) Inventors: Ryotaro Kojima, Saitama (JP); Koichi Nakamaru, Saitama (JP); Tokutarou Yasue, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/223,584

(22) PCT Filed: Feb. 5, 2007

(86) PCT No.: PCT/JP2007/051887
§ 371 (c)(1),
(2), (4) Date: Aug. 4, 2008

(87) PCT Pub. No.: WO2007/091501
PCT Pub. Date: Aug. 16, 2007

(65) Prior Publication Data
US 2009/0137685 A1    May 28, 2009

(30) Foreign Application Priority Data
Feb. 6, 2006  (JP) .................................. 2006-027883

(51) Int. Cl.
*A61K 31/137* (2006.01)
(52) U.S. Cl. ..................................................... 514/653
(58) Field of Classification Search .................. None
See application file for complete search history.

(56) References Cited

U.S. PATENT DOCUMENTS

| | | | |
|---|---|---|---|
| 5,447,922 A | 9/1995 | Lawrence et al. | |
| 5,604,229 A | 2/1997 | Fujita et al. | |
| 5,948,820 A | 9/1999 | Fujita et al. | |
| 6,004,565 A | 12/1999 | Chiba et al. | |
| 6,214,873 B1 | 4/2001 | Adachi et al. | |
| 6,489,331 B1 | 12/2002 | Shimada et al. | |
| 6,960,692 B2 | 11/2005 | Kohno et al. | |
| 6,963,012 B2 | 11/2005 | Kohno et al. | |
| 7,456,157 B2 | 11/2008 | Kohno et al. | |
| 7,482,491 B2 | 1/2009 | Kohno et al. | |
| 7,807,854 B2 * | 10/2010 | Kudou et al. | 564/336 |
| 2002/0040050 A1 | 4/2002 | Xu et al. | |
| 2002/0091105 A1 | 7/2002 | Mandala et al. | |
| 2002/0143034 A1 | 10/2002 | Taniguchi et al. | |
| 2003/0236297 A1 | 12/2003 | Nishi et al. | |
| 2004/0058894 A1 | 3/2004 | Doherty et al. | |
| 2004/0067908 A1 | 4/2004 | Nakade et al. | |
| 2004/0087662 A1 | 5/2004 | Bigaud et al. | |
| 2004/0110728 A1 | 6/2004 | Macdonald et al. | |
| 2004/0138462 A1 | 7/2004 | Sakurai et al. | |
| 2004/0147490 A1 | 7/2004 | Albert et al. | |
| 2004/0224941 A1 | 11/2004 | Seko et al. | |
| 2004/0235794 A1 | 11/2004 | Nakade et al. | |
| 2004/0242654 A1 | 12/2004 | Kohno et al. | |
| 2004/0248952 A1 | 12/2004 | Pan et al. | |
| 2004/0254222 A1 | 12/2004 | Kohno et al. | |
| 2005/0009786 A1 | 1/2005 | Pan et al. | |
| 2005/0020837 A1 | 1/2005 | Doherty et al. | |
| 2005/0033055 A1 | 2/2005 | Bugianesi et al. | |
| 2005/0043386 A1 | 2/2005 | Nishi et al. | |
| 2005/0107345 A1 | 5/2005 | Doherty et al. | |
| 2005/0222422 A1 | 10/2005 | Lynch et al. | |
| 2005/0245575 A1 | 11/2005 | Chen et al. | |
| 2006/0046979 A1 | 3/2006 | Foster et al. | |
| 2006/0089334 A1 | 4/2006 | Budhu et al. | |
| 2006/0135622 A1 | 6/2006 | Kohno et al. | |
| 2006/0135786 A1 | 6/2006 | Saha et al. | |

(Continued)

FOREIGN PATENT DOCUMENTS

GB        2 400 318 A    10/2004

(Continued)

OTHER PUBLICATIONS

Vippagunta et al., Advanced Drug Delivery Reviews, 48 (2001), pp. 3-26.*
The Merck Manual, 17$^{th}$ edition (1999), pp. 302-307.*
International Search Report issued Mar. 13, 2007 in the International (PCT) Application PCT/JP2007/051887 of which the present application is the U.S. National Stage.
English version of International Preliminary Report on Patentability issued Aug. 21, 2008 in the International (PCT) Application PCT/JP2007/051887 of which the present application is the U.S. National Stage.
Yasuyuki Deguchi et al., "Effects of FTY720 on DSS-induced enteritis in mice", Presented at Area 15, Kobe International Exhibition Hall, Building 1, 2nd floor, Oct. 6, 2005, Japanese Society of Gastroenterology (abstract).

(Continued)

*Primary Examiner* — Phyllis G. Spivack
(74) *Attorney, Agent, or Firm* — Wenderoth, Lind & Ponack, L.L.P.

(57) ABSTRACT

A novel therapeutic and prophylactic agent for inflammatory bowel diseases and a method for treating inflammatory bowel diseases is provided. The agent comprises a 2-amino-1,3-propanediol derivative (e.g., 2-amino-2-[4-(3-benzyloxyphenylthio)-2-chlorophenyl]ethyl-1,3-propanediol hydrochloride) represented by the chemical formula (1) or a pharmaceutically acceptable salt or hydrate thereof:

(Chemical formula 1)

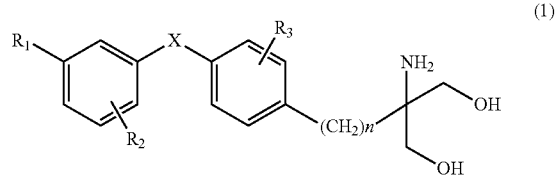

(1)

The agent is useful in the treatment or prevention of Crohn's disease, Crohn's disease in large intestine, intestinal Behcet's disease, ulcerative colitis, bleeding rectal ulcer and pouchitis.

14 Claims, No Drawings

U.S. PATENT DOCUMENTS

| | | | |
|---|---|---|---|
| 2006/0148830 A1 | 7/2006 | Terakado et al. |
| 2006/0148844 A1 | 7/2006 | Nakade et al. |
| 2006/0160771 A1 | 7/2006 | Kohno et al. |
| 2006/0161005 A1 | 7/2006 | Doherty et al. |
| 2006/0166940 A1 | 7/2006 | Buehlmayer et al. |
| 2006/0211656 A1 | 9/2006 | Albert et al. |
| 2006/0211658 A1 | 9/2006 | Hinterding et al. |
| 2006/0252741 A1 | 11/2006 | Colandrea et al. |
| 2006/0264403 A1 | 11/2006 | Albert |
| 2007/0010494 A1 | 1/2007 | Ehrhardt et al. |
| 2007/0043014 A1 | 2/2007 | Doherty et al. |
| 2007/0088002 A1 | 4/2007 | Lynch et al. |
| 2007/0135501 A1 | 6/2007 | Hinterding et al. |
| 2007/0149597 A1 | 6/2007 | Nishi et al. |
| 2007/0167410 A1 | 7/2007 | Pan et al. |
| 2007/0167425 A1 | 7/2007 | Nakade et al. |
| 2007/0191468 A1 | 8/2007 | Nishi et al. |
| 2007/0203100 A1 | 8/2007 | Pan et al. |
| 2007/0225260 A1 | 9/2007 | Hinterding et al. |
| 2008/0025973 A1 | 1/2008 | Fleenor et al. |
| 2008/0027508 A1 | 1/2008 | Chu |
| 2008/0032923 A1 | 2/2008 | Kudou et al. |
| 2008/0153882 A1 | 6/2008 | Nishi et al. |
| 2008/0161410 A1 | 7/2008 | Kusters et al. |
| 2008/0200438 A1 | 8/2008 | Albert et al. |
| 2008/0207584 A1 | 8/2008 | Habashita et al. |
| 2008/0207941 A1 | 8/2008 | Tsubuki et al. |
| 2008/0249093 A1 | 10/2008 | Colandrea et al. |
| 2009/0023797 A1 | 1/2009 | Azzaoui et al. |

FOREIGN PATENT DOCUMENTS

| | | |
|---|---|---|
| JP | 2002-53575 | 2/2002 |
| JP | 2002-316985 | 10/2002 |
| JP | 2003-137894 | 5/2003 |
| JP | 2003-267936 | 9/2003 |
| JP | 2004-137208 | 5/2004 |
| JP | 2004-307439 | 11/2004 |
| JP | 2004-307440 | 11/2004 |
| JP | 2004-307441 | 11/2004 |
| JP | 2004-307442 | 11/2004 |
| JP | 2005-47899 | 2/2005 |
| JP | 2005-247691 | 9/2005 |
| WO | 01/98301 | 12/2001 |
| WO | 2005/014525 | 2/2005 |
| WO | 2005/014603 | 2/2005 |
| WO | 2005/063671 | 7/2005 |
| WO | 2005/105146 | 11/2005 |
| WO | 2006/041015 | 4/2006 |
| WO | 2006/063033 | 6/2006 |
| WO | 2006/129688 | 12/2006 |
| WO | 2007/043433 | 4/2007 |
| WO | 2007/043568 | 4/2007 |
| WO | 2007/091501 | 8/2007 |

OTHER PUBLICATIONS

Poster Session of Shiga University of Medical Science, Presented at Area 15, Kobe International Exhibition Hall, Building 1, 2nd floor, Oct. 6, 2005.

Supplementary European Search Report issued Feb. 16, 2010 in corresponding European Application No. 07713815.4-2123.

Yasushi, Kohno et al., "*Discovery of KRP-203, A potent and orally active new type of immunosuppressant, Sphingosine-1-phosphate receptor agonist*", American Chemical Society, National meeting, American Chemical Society, Washington, D.C., vol. 229, No. Part 2, Mar. 1, 2005, pp. U150, XP008071718.

Daniel, Carolin, et al., "*Therapeutic effects of the new lymphocyte homing reagent FTY720 in TNBS-cokitis*", Gastroenterology, vol. 128, No. 4, Suppl. 2, Apr. 2005, pp. A199, XP009128860.

Blam et al., Integrating Anti-Tumor Necrosis Factor Therapy in Inflammatory Bowel Disease: Current and Future Perspectives, Am. J. Gastroenterology, 2001, vol. 96, No. 7, pp. 1977-1997.

Keller et al., Immunomodulator FTY720 Induces Myofibroblast Differentiation via the Lysophospholipid Receptor S1P3 and Smad3 Signaling, Am. J. Pathology, Jan. 2007, vol. 170, No. 1, pp. 281-292.

Yasuyuki Igarashi, Sphingosine-1-Phosphate as an Intercellular Signaling Molecule, Ann. NY Acad. Sci., 1998, vol. 845, pp. 19-31.

Jacobs et al., Intramuscular Interferon Beta-1a for Disease Progression in Relapsing Multiple Sclerosis, Ann. Neurol., 1996, vol. 39, No. 3, pp. 285-294.

Weinshenker et al., A Randomized Trial of Plasma Exchange in Acute Central Nervous System Inflammatory Demyelinating Disease, Ann. Neurol., 1999, vol. 46, No. 6, pp. 878-886.

Ganem et al., The Molecular Biology of the Hepatitis B Virus, Annu. Rev. Biochem., 1987, vol. 56 pp. 651-693.

Kaneko et al., Sphingosine-1-phosphate receptor agonists suppress concanavalin A-induced hepatic injury in mice, Biochem. and Biophys. Res. Commun., 2006, vol. 345, pp. 85-92.

Okazaki et al., Molecular Cloning of a Novel Putative G Protein-Coupled Receptor Expressed in the Cardiovascular System, Biochem. and Biophys. Res. Commun., 1993, vol. 190, No. 3, pp. 1104-1106.

Klein et al., Total Synthesis and Antifungal Evaluation of Cyclic Aminohexapeptides, Bioorg. Med. Chem., 2000, vol. 8, pp. 167-1696.

Hashimoto et al., β-Phenylselenoalanine as a dehydroalanine precursor-efficient synthesis of alternariolide (AM-toxin I), Chem. Commun., 1996, pp. 1139-1140.

Levkau et al., High-Density Lipoprotein Stimulates Myocardial Perfusion in Vivo, Circulation, 2004, vol. 110, pp. 3355-3359.

Salomone et al., $S1P_3$ receptors mediate the potent constriction of cerebral arteries by sphingosine-1-phosphate, Eur. J. Pharmacol., 2003, vol. 469, pp. 125-134.

Heneghan et al., Current and Novel Immunosuppressive Therapy for Autoimmune Hepatitis, Hepatology, 2002, vol. 35, No. 1, pp. 7-13.

Francis V. Chisari, Cytotoxic T Cells and Viral Hepatitis, J. Clin. Invest., Apr. 1997, vol. 99, No. 7, pp. 1472-1477.

Kiuchi et al., Synthesis and Immunosuppressive Activity of 2-Substituted 2-Aminopropane-1,3-diols and 2-Aminoethanols, J. Med. Chem., 2000, vol. 43, pp. 2946-2961.

Brinkmann et al., The Immune Modulator FTY720 Targets Sphingosine 1-Phosphate Receptors, J. Biol. Chem., 2002, vol. 277, No. 24, pp. 21453-21457.

Sanna et al., Sphingosine 1-Phosphate (S1P) Receptor Subtypes $S1P_1$ and $S1P_3$, Respectively, Regulate Lymphocyte Recirculation and Heart Rate, J. Biol. Chem., Apr. 2 2004, vol. 279, No. 14, pp. 13839-13848.

Forrest et al., Immune Cell Regulation and Cardiovascular Effects of Sphingosine 1-Phosphate Receptor Agonists in Rodents are Mediated via Distinct Receptor Subtypes, J. Pharm. Exp. Ther., 2004, vol. 309, No. 2, pp. 758-768.

George C. Ebers, Randomised double-blind placebo-controlled study of interferon β-1a in relapsing/remitting multiple sclerosis, Lancet, Nov. 7, 1998, vol. 352, pp. 1498-1501.

Takuwa et al., Subtype-specific, differential activities of the EDG family receptors for sphingosine-1-phosphate, a novel lysophospholipid mediator, Mol. Cell. Endocrinol., 2001, vol. 177, pp. 3-11.

Fried et al., Peginterferon Alfa-2a Plus Ribavirin for Chronic Hepatitis C Virus Infection, N. Engl. J. Med., Sep. 26, 2002, vol. 347, No. 13, pp. 975-982.

Mailliard et al., Suppressing Hepatitis B without Resistance—So Far, So Good, N. Engl. J. Med., Feb. 27, 2003, vol. 348, No. 9, pp. 848-850.

Niessen et al., Dentritic cell PAR1-S1P3 signalling couples coagulation and inflammation, Nature, Apr. 3, 2008, vol. 452, No. 3, pp. 654-658.

IFNB Multiple Sclerosis Study Group, Interferon beta-1b is effective in relapsing-remitting multiple sclerosis. I. Clinical results of a multicenter, randomized, double-blind, placebo-controlled trial, Neurology, Apr. 1993, vol. 43, pp. 655-661.

Paty et al., Interferon beta-1b is effective in relapsing-remitting multiple sclerosis. II. MRI analysis results of a multicenter, randomized, double-blind, placebo-controlled trial, Apr. 1993, vol. 43, pp. 662-667.

Johnson et al., Copolymer 1 reduces relapse rate and improves disability in relapsing-remitting multiple sclerosis: Results of a phase III multicenter, double-blind, placebo-controlled trial, Neurology, Jul. 1995, vol. 45, pp. 1268-1276.

Zivadinov et al., Effects of IV methylprednisolone on brain atrophy in relapsing-remitting MS, Neurology, 2001, vol. 57, pp. 1239-1247.

Goodin et al., Disease modifying therapies in multiple sclerosis; Report of the Therapeutics and Technology Assessment Subcommittee of the American Academy of Neurology and the MS Council for Clinical Practice Guidelines, Neurology, 2002, vol. 58, pp. 169-178.

Rudick et al., Management of Multiple Cclerosis, N. Engl. J. Med., Nov. 27, 1997, vol. 337, No. 22, pp. 1604-1611.

Daniel K. Podolsky, Inflammatory Bowel Disease, N. Engl. J. Med., Aug. 8, 2002, vol. 347, No. 6, pp. 417-429.

Kappos et al., Oral Fingolimod (FTY720) for Relapsing Multiple Sclerosis, N. Engl. J. Med., Sep. 14, 2006, vol. 355, No. 11, pp. 1124-1140.

Viscido et al., Inflammatory bowel diseases: clinical update of practical guidelines, Nucl. Med. Commun., 2005, vol. 26, No. 7, pp. 649-655.

Gon et al., $S1P_3$, receptor-induced reorganization of epithelial tight junctions comprises lung barrier integrity and is potentiated by TNF, PNAS, Jun. 28, 2005, vol. 102, No. 26, pp. 9270-9275.

Saito et al., Hepatitis C virus infection is associated with the development of hepatocellular carcinoma, Proc. Natl. Acad. Sci. USA, Sep. 1990, vol. 87, pp. 6547-6549.

Mandala et al., Alteration of Lymphocyte Trafficking by Sphingosine-1-Phosphate Receptor Agonists, Science, Apr. 2, 2002, vol. 296, pp. 346-349.

Hinterding et al., Synthesis of Chiral Analogues of FTY720 and its Phosphate, Synthesis, 2003, No. 11, pp. 1667-1670.

Campbell et al., The Synthesis of Novel Amino Acids via Hydroboration-Suzuki Cross Coupling, Tetrohedron Letters, 1999, vol. 40, pp. 5263-5266.

Collier et al., The direct synthesis of novel enantiomerically pure α-amino acids in protected form via suzuki cross-coupling, Tetrahedron Letters, 2000, vol. 41, pp. 7115-7119.

Long et al., Enantioselective syntheses of homophenylalanine derivatives via nitron 1,3-dipolar cycloaddition reactions with styrenes, Tetrahedron Letters, 2001, vol. 42, pp. 5343-5345.

Shimizu et al., KRP-203, a Novel Synthetic Immunosuppressant, Prolongs Graft Survival and Attenuates Chronic Rejection in Rat Skin and Heart Allografts, Circulation, 2005, vol. 111, pp. 222-229.

Takahashi et al., A Novel Immunomodulator KRP-203 Combined with Cyclosporine Prolonged Graft Survival and Abrogated Transplant Vasculopathy in Rat Heart Allografts, Transplant. Proc., 2005, vol. 37, pp. 143-145.

Julien Davaille et al., "Sphingosine 1-Phosphate Triggers Both Apoptotic and Survival Signals for Human Hepatic Myofibroblasts", J. Biol. Chem., vol. 277, No. 40, pp. 37323-37330 (2002).

Supplementary European Office Action issued Feb. 16, 2010 in corresponding European Application No. 07713815.4-2123.

Uraushihara, Koji, et al., "Regulation of Murine Inflammatory Bowel Disease by CD25+ and CD25-31 CD4+ Glucocorticoid-Induced TNF Receptor Family-Related Gene+ Regulatory T Cells", The Journal of Immunology, 2003, pp. 708-716.

Santucci, Luca, et al., "Different Sensitivity of Lamina Propria T-Cell Subsets to Nitric Oxide-Induced Apoptosis Explains Immunomodulatory Activity of a Nitric Oxide-Releasing Derivative of Mesalamine in Rodent Colitis", Gastroenterology, 2005, vol. 128, No. 5, pp. 1243-1257.

* cited by examiner

METHOD FOR TREATING AN INFLAMMATORY BOWEL DISEASE USING 2-AMINO-2-[4-(3-BENZYLOXYPHENYLTHIO)-2-CHLOROPHENYL]ETHYL-1,3-PROPANEDIOL OR A SALT THEREOF

TECHNICAL FIELD

The present invention relates to a therapeutic agent for inflammatory bowel diseases that contains, as an active ingredient, 2-amino-1,3-propanediol derivative, a sphingosine-1-phosphate receptor agonist, or a pharmaceutically acceptable salt or hydrate thereof. The present invention also relates to a method for treating inflammatory bowel diseases.

BACKGROUND ART

Inflammatory bowel diseases, represented by Crohn's disease and ulcerative colitis, are intractable diseases that often develop at relatively young ages and cause abdominal pain, fever, diarrhea, hematochezia and other symptoms. Crohn's disease is a granulomatous inflammatory disease of unknown cause that affects any part of the gastrointestinal tract from mouth to anus in a discontinuous manner. The disease progresses from ulcer to fibrosis and stricture, involving all layers of the bowel wall from mucosa to serosa. It is associated with systemic symptoms such as abdominal pain, chronic diarrhea, fever and malnutrition. On the other hand, ulcerative colitis is characterized by diffuse nonspecific inflammation of the large intestine of unknown cause. The disease primarily affects mucosa and often forms erosions and ulcers. It is also associated with various systemic symptoms including bloody diarrhea. Inflammatory bowl disease also refers to other inflammatory disorders in small and large intestines, including intestinal Behcet's disease, ulcerative colitis, bleeding rectal ulcer and pouchitis. Although it is believed that the etiology of inflammatory bowel diseases involves abnormal immune function, the exact cause of the diseases still remains unknown (Non-Patent Documents 1 and 2).

Medications for inflammatory bowel diseases include immunosuppressors, steroids, salazosulfapyridine and mesalazine. While immunosuppressors, in particular antimetabolites such as azathiopurine and 6-mercaptopurine, are considered effective against Crohn's disease, the drugs exhibit low efficacy at an early stage of administration and often cause allergies, pancreatitis, leukopenia and other side effects. High doses of cyclosporine are effective against inflammatory and fistulous diseases, but the drug cannot be used for a prolonged period due to its toxicity. Infliximab, a monoclonal antibody that inhibits a tumor necrosis factor, is administered by intravenous infusion to treat moderate or serious Crohn's disease (especially those accompanied by fistula) resistant to other treatments. However, long-term effects and side effects of the treatment are unknown. Other potential immunosuppressors include interleukin-1 blockers, anti-interleukin-12 antibodies, anti-CD4 antibodies, adhesive molecule inhibitors, and monoclonal antibodies against down-regulatory cytokines and tumor necrosis factors. Each of the current therapeutic approaches for the treatment of inflammatory bowel diseases has its own disadvantages. Thus, there is a need for more effective and safe medications (Non-Patent Documents 3, 4 and 5).

2-amino-1,3-propanediol derivatives described in the present application are known as effective immunosuppressors used to prevent rejection in organ transplantation (Patent Literatures No. 1 and 2). While 2-amino-1,3-propanediol derivatives have been known to act as sphingosine-1-phosphate receptor agonists, their usefulness in the treatment of inflammatory bowel diseases has never been described.

[Non-Patent Document 1] 1997 Annual Report by the Research Committee of Intractable Inflammatory Bowel Disorders: The Ministry of Health and Welfare of Japan.
[Non-Patent Document 2] New Engl J Med, 2002, 347: 417-429
[Non-Patent Document 3] Am J Gastroenterol, 2001, 96: 1977-1997
[Non-Patent Document 4] Nucl Med Commun, 2005, 26:649-655
[Non-Patent Document 5] Saishin Igaku 2004, 59:1070-1075
[Patent Document 1] WO2003/029184 Pamphlet
[Patent Document 2] WO2003/029205 Pamphlet

DISCLOSURE OF THE INVENTION

Problems to Be Solved by the Invention

It is an objective of the present invention to provide a therapeutic agent for the treatment of inflammatory bowel diseases that contains, as an active ingredient, a 2-amino-1,3-propanediol derivative, or a pharmaceutically acceptable salt or hydrate thereof It is another objective to provide a method for treating inflammatory bowel diseases.

Means for Solving the Problems

The present inventors discovered that a 2-amino-1,3-propanediol derivative, a sphingosine-1-phosphate receptor agonist, or a pharmaceutically acceptable salt or hydrate thereof is useful in the treatment or prevention of inflammatory bowel diseases (Crohn's disease, Crohn's disease in large intestine, intestinal Behcet's disease, ulcerative colitis, bleeding rectal ulcer and pouchitis) and thus devised the present invention.

Specifically, the present invention concerns the following:
1) A therapeutic or prophylactic agent for an inflammatory bowel disease containing, as an active ingredient, a 2-amino-1,3-propanediol derivative represented by the chemical formula (1):

(Chemical formula 1)

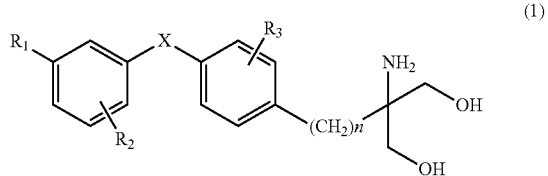

(1)

[wherein $R_1$ is a halogen atom, a trihalomethyl group, a hydroxy group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group or a benzyloxy group; $R_3$ is a hydrogen atom, a halogen atom, a trifluoromethyl group, a lower alkoxy group having 1 to 4 carbon atoms, a hydroxy group, a benzyloxy group, a lower alkyl group having 1 to 7 carbon atoms, a phenyl group, a lower alkoxymethyl group having 1 to 4 carbon atoms or a lower alkylthio group having 1 to 4 carbon atoms; X is O, S, SO or $SO_2$; and n is an integer from 1 to 4], or a pharmaceutically acceptable salt or hydrate thereof.

2) The therapeutic or prophylactic agent for an inflammatory bowel disease according to 1), wherein the compound represented by the chemical formula (1) is 2-amino-2-[4-(3-benzyloxyphenylthio)-2-chlorophenyl]ethyl-1,3-propanediol.

3) The therapeutic or prophylactic agent for an inflammatory bowel disease according to 1), wherein the compound represented by the chemical formula (1) is a hydrochloride of 2-amino-2-[4-(3-benzyloxyphenylthio)-2-chlorophenyl]ethyl-1,3-propanediol.

4) The therapeutic or prophylactic agent for an inflammatory bowel disease according to 1) to 3), wherein the inflammatory bowel disease is Crohn's disease, Crohn's disease in large intestine, intestinal Behcet's disease, ulcerative colitis, bleeding rectal ulcer, or pouchitis.

5) A method for treating an inflammatory bowel disease, using as an active ingredient a 2-amino-1,3-propanediol derivative represented by the chemical formula (1):

(Chemical formula 2)

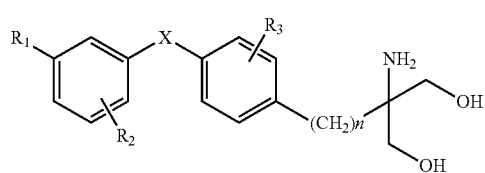
(1)

[wherein $R_1$ is a halogen atom, a trihalomethyl group, a hydroxy group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group or a benzyloxy group; $R_3$ is a hydrogen atom, a halogen atom, a trifluoromethyl group, a lower alkoxy group having 1 to 4 carbon atoms, a hydroxy group, a benzyloxy group, a lower alkyl group having 1 to 7 carbon atoms, a phenyl group, a lower alkoxymethyl group having 1 to 4 carbon atoms or a lower alkylthio group having 1 to 4 carbon atoms; X is O, S, SO or $SO_2$; and n is an integer from 1 to 4], or a pharmaceutically acceptable salt or hydrate thereof.

6) The method for treating an inflammatory bowel disease according to 5), wherein the inflammatory bowel disease is Crohn's disease, Crohn's disease in large intestine, intestinal Behcet's disease, ulcerative colitis, bleeding rectal ulcer, or pouchitis.

7) A therapeutic or prophylactic agent for an inflammatory bowel disease, comprising a 2-amino-1,3-propanediol derivative represented by the general formula (1):

(Chemical formula 3)

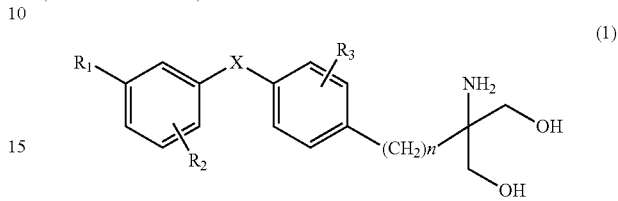
(1)

[wherein $R_1$ is a halogen atom, a trihalomethyl group, a hydroxy group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group or a benzyloxy group; $R_3$ is a hydrogen atom, a halogen atom, a trifluoromethyl group, a lower alkoxy group having 1 to 4 carbon atoms, a hydroxy group, a benzyloxy group, a lower alkyl group having 1 to 7 carbon atoms, a phenyl group, a lower alkoxymethyl group having 1 to 4 carbon atoms or a lower alkylthio group having 1 to 4 carbon atoms; X is O, S, SO or $SO_2$; and n is an integer from 1 to 4] or a pharmaceutically acceptable salt or hydrate thereof, in combination of at least one therapeutic agent for an inflammatory bowel disease.

8) The therapeutic or prophylactic agent for an inflammatory bowel disease according to 7), wherein the at least one therapeutic agent for an inflammatory bowel disease comprises a sulfasalazine, a steroid, or an immunosuppressor.

Advantages of the Invention

According to the present invention, there is provided a therapeutic or prophylactic agent for inflammatory bowel diseases that contains, as an active ingredient, a diarylsulfide or diarylether derivative having a 2-amino-1,3-propanediol structure, or a pharmaceutically acceptable salt or hydrate thereof. The diarylsulfide or diarylether derivative acts as a sphingosine-1-phosphate receptor agonist. There is also provided a method for treating or preventing inflammatory bowel diseases, including Crohn's disease, Crohn's disease in large intestine, intestinal Behcet's disease, ulcerative colitis, bleeding rectal ulcer, or pouchitis.

BEST MODE FOR CARRYING OUT THE INVENTION

The 2-amino-1,3-propanediol derivatives of the present invention are sphingosine-1-phosphate receptor agonists and comprise a group of compounds represented by the chemical formula (1) and pharmaceutically acceptable salts and hydrates thereof:

(Chemical formula 4)

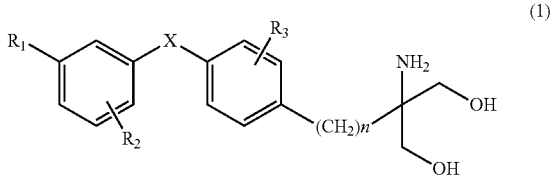

(1)

[wherein $R_1$ is a halogen atom, a trihalomethyl group, a hydroxy group, a lower alkyl group having 1 to 7 carbon atoms, a substituted or unsubstituted phenyl group, an aralkyl group, a lower alkoxy group having 1 to 4 carbon atoms, a trifluoromethyloxy group, a phenoxy group, a cyclohexylmethyloxy group, a substituted or unsubstituted aralkyloxy group, a pyridylmethyloxy group, a cinnamyloxy group, a naphthylmethyloxy group, a phenoxymethyl group, a hydroxymethyl group, a hydroxyethyl group, a lower alkylthio group having 1 to 4 carbon atoms, a lower alkylsulfinyl group having 1 to 4 carbon atoms, a lower alkylsulfonyl group having 1 to 4 carbon atoms, a benzylthio group, an acetyl group, a nitro group or a cyano group; $R_2$ is a hydrogen atom, a halogen atom, a trihalomethyl group, a lower alkoxy group having 1 to 4 carbon atoms, a lower alkyl group having 1 to 7 carbon atoms, a phenethyl group or a benzyloxy group; $R_3$ is a hydrogen atom, a halogen atom, a trifluoromethyl group, a lower alkoxy group having 1 to 4 carbon atoms, a hydroxy group, a benzyloxy group, a lower alkyl group having 1 to 7 carbon atoms, a phenyl group, a lower alkoxymethyl group having 1 to 4 carbon atoms or a lower alkylthio group having 1 to 4 carbon atoms; X is O, S, SO or $SO_2$; and n is an integer from 1 to 4].

The term "halogen atom" in the chemical formula (1) of the present invention includes a fluorine atom, a chlorine atom, a bromine atom and an iodine atom. The term "trihalomethyl group" includes a trifluoromethyl group and a trichloromethyl group. The term "lower alkyl group having 1 to 7 carbon atoms" includes straight-chained or branched hydrocarbons having 1 to 7 carbon atoms, such as methyl, ethyl, propyl, isopropyl, butyl, t-butyl, pentyl, hexyl and heptyl.

The term "substituted or unsubstituted phenoxy group" includes those in which the benzene ring has at any position a halogen atom, such as a fluorine atom, a chlorine atom, a bromine atom and an iodine atom, a trifluoromethyl group, a lower alkyl group having 1 to 4 carbon atoms or a lower alkoxy group having 1 to 4 carbon atoms. The term "aralkyl group" as in "aralkyl group" and "aralkyloxy group" includes a benzyl group, a diphenylmethyl group, a phenethyl group and phenylpropyl group. The term "lower alkyl group" in "lower alkoxy group having 1 to 4 carbon atoms," "lower alkylthio group having 1 to 4 carbon atoms," "lower alkylsufinyl group having 1 to 4 carbon atoms," and "lower alkylsulfonyl group having 1 to 4 carbon atoms" includes straight-chained or branched hydrocarbons having 1 to 4 carbon atoms, such as methyl, ethyl, propyl, isopropyl and butyl. The term "substituted or unsubstituted aralkyl group" includes those in which the benzene ring has at any position a halogen atom, such as a fluorine atom, a chlorine atom, a bromine atom and an iodine atom, a trifluoromethyl group, a lower alkyl group having 1 to 4 carbon atoms or a lower alkoxy group having 1 to 4 carbon atoms.

Examples of pharmaceutically acceptable salts of the compound of the chemical formula (1) of the present invention include acid-addition salts such as hydrochlorides, hydrobromides, acetates, trifluoroacetates, methanesulfonates, citrates and tartrates.

More specific examples of the compound of the general formula (1) are 2-amino-2-[4-(3-benzyloxyphenylthio)-2-chlorophenyl] ethyl-1,3-propanediol and hydrochlorides thereof.

The compounds of the general formula (1) of the present invention are described in, for example, WO03/029184 pamphlet and WO03/029205 pamphlet and can be produced by techniques described in these publications.

The thus-obtained compounds of the present invention or pharmaceutically acceptable salts and hydrates thereof are useful in the treatment of inflammatory bowel diseases. The therapeutic agents of the present invention are administered systemically or topically and orally or parenterally. The compounds may be formulated as oral or parenteral preparations depending on their properties. Specifically, the active ingredients may be mixed with pharmaceutically acceptable carriers, excipients, binders, diluents or other auxiliary agents and formulated as granules, powders, tablets, capsules, syrups, suppositories, suspensions, solutions and other dosage forms. While the compounds may be administered in different doses depending on their use, the weight, age and conditions of the patients, they are typically administered in a single dose of 0.01 to 100 mg/patient, preferably at a single dose of 0.1 to 5 mg/patient, once to three times a day.

These preparations may be used in combination with at least one drug used to treat inflammatory bowel diseases. Examples of such drugs include sulfasalazines, steroids and immunosuppressors.

Examples of sulfasalazines include mesalazine, olsalazine, sulfasalazine and balsalazide. Examples of steroids include hydrocortisone, methylprednisolone, budesonide and betamethasone phosphate. Examples of immunosuppressors include azathioprine, 6-mercaptopurine, cyclosporine, tacrolimus, anti-TNF-α antibody and anti-α4 integrin antibody.

EXAMPLES

The present invention will now be described with reference to examples. While these examples primarily concern 2-amino-2-[4-(3-benzyloxyphenylthio)-2-chlorophenyl] ethyl-1,3-propanediol hydrochloride (which may be referred to as "KRP-203," hereinafter), one of the compounds represented by the chemical formula (1), other compounds are also encompassed by the present invention and the scope of the invention is by no means limited by these examples.

Example 1

Therapeutic Effects on Dextran Sodium Sulfate-Induced Colitis in Mice

Colitis was induced in BALB/C male mice by allowing animals To drink a 5% aqueous solution of dextran sodium sulfate (DSS) (average molecular weight=5000) for 7 days [Kitajima, S. et. al., Exp Anim, Vol. 49, No. 1: 9-15 (2000)]. KRP-203 dissolved in distilled water (at 0.01, 0.03 and 0.1 mg/kg) was orally administered once a day for 8 days, starting the day before the administration of DSS solution. One group was administered distilled water as a placebo.

8 days after the start of the DSS period, mice were anesthetized With diethylether and sacrificed by cervical dislocation. The large intestine (the segment from colon to anus) was removed from each animal. Because it is known that the ingestion of DSS solution causes colitis in mice that causes a decrease in the length of large intestine [Okayasu, I. et. al., Gastroenterology, Vol. 98: 694-702 (1990)], the length of the large intestine from the colon to anus was measured with a caliper. The large intestine was then cut open longitudinally to expose the lumen and the content was washed off with physiological saline. The specimens were assayed and compared for the activity of myeloperoxidase, a marker of inflammation in colitis [Grisham, M B. et. al., Methods Enzymol, Vol. 186: 729-742 (1990)].

The comparison of the length of large intestine is shown in Table 1. The results indicate that KRP-203 significantly reduced the colitis-induced decrease in the length of large intestine.

TABLE 1

Reduction of the decrease in the length of large intestine by KRP-203

| Groups tested | Number of Samples | Length of large intestine (mm) |
|---|---|---|
| Placebo group | 8 | 64.7 ± 1.7## |
| 0.01 mg/kg KRP-203 group | 10 | 67.4 ± 1.4 |
| 0.03 mg/kg KRP-203 group | 10 | 72.7 ± 1.5** |
| 0.1 mg/kg KRP-203 group | 9 | 71.4 ± 1.4* |
| Normal group | 4 | 84.7 ± 2.2 |

Data are given in average ± standard error.
$p < 0.01$ (Student's t-test on normal group)
*$p < 0.05$ (Dunnett's test on placebo group)
**$p < 0.01$ (Dunnett's test on placebo group)

The results of the assay for myeloperoxidase activity in large intestine are shown in Table 2. The results indicate that KRP-203 significantly reduced the colitis-induced increase in the myeloperoxidase activity in large intestine.

TABLE 2

Suppression of the increase in myeloperoxidase activity in large intestine by KRP-203

| Groups tested | Number of Samples | myeloperoxidase activity (U/g protein) |
|---|---|---|
| Placebo group | 8 | 108.2 ± 20.7## |
| 0.01 mg/kg KRP-203 group | 10 | 55.8 ± 16.2* |
| 0.03 mg/kg KRP-203 group | 10 | 36.8 ± 5.9** |
| 0.1 mg/kg KRP-203 group | 9 | 44.4 ± 6.4** |
| Normal group | 4 | 5.0 ± 0.1 |

Data are given in average ± standard error.
$p < 0.01$ (Aspin-Welch's t-test on normal group)
*$p < 0.05$ (Dunnett's test on placebo group)
**$p < 0.01$ (Dunnett's test on placebo group)

DDS-induced colitis in mice is frequently used as a disease model of inflammatory bowel diseases in humans [Elson, C O. et. al., Gastroenterology, Vol. 109: 1344-1367 (1995); Hibi, T. et. al., J Gastroenterol, Vol. 37: 409-417 (2002)]. Thus, these results demonstrate the usefulness of KRP-203 in the treatment of inflammatory bowel diseases.

Example 2

Comparative Example

Several drugs are used in the treatment of inflammatory bowel diseases. Immunosuppressors, drugs used to prevent rejection in organ transplantation, are one such option. As with KRP-203, two representative immunosuppressors cyclosporine and tacrolimus were examined for their effects.

Cyclosporine was dissolved in soybean oil (at 10 and 30 mg/kg) and was orally administered once a day for 8 days, starting the day before the start of the DSS period. One group was administered soybean oil as a placebo. The increase in the myeloperoxidase activity in large intestine was suppressed by 54% in the 10 mg/kg group and by 73% in the 30 mg/kg group as compared to the placebo group.

Tacrolimus was suspended in a 0.5% aqueous solution of carboxymethylcellulose sodium (CMC-Na) (at 3 mg/kg) and was administered once a day for 8 days, starting the day before the start of the DSS period. One group was administered 0.5% aqueous CMC-Na solution as a placebo. The increase in the myeloperoxidase activity in large intestine was suppressed by 37% in the 3 mg/kg group as compared to the placebo group.

The effect on DDS-induced colitis in mice was then compared between cyclosporine and tacrolimus, two representative immunosuppressors, and KRP-203: The increase in the myeloperoxidase activity in large intestine was suppressed by administration of KRP-203 by 51% in the 0.01 mg/kg group, by 69% in the 0.03 mg/kg group, and by 62% in the 0.1 mg/kg group as compared to the placebo group (Table 2). These results suggest that lesser doses of KRP-203 have a comparable or greater therapeutic effect on inflammatory bowel diseases than cyclosporine and tacrolimus.

Example 3

Effect of KRP-203 on IL-10 Knockout Mice

B6.129P2-IL10$^{<tm1Cgn>}$/J (IL-10 knockout) mice (male, 5-6 week old) were obtained for the test. KRP-203 dissolved in distilled water was orally administered at a dose of 0.1 mg/kg once a day for 4 weeks, starting 8 weeks after the animals were obtained. One group was administered distilled water alone as a placebo. Following the administration period, the animals were dissected to remove large intestine, which was then fixed in formalin. Subsequently, tissue slices were prepared from the formalin-fixed large intestine and were stained with hematoxylin and eosin. The proximal, middle, and distal segments of the large intestine were then histologically scored according to the standard procedure (Berg D J, et al., Gastroenterology, 123: 1527-1542 (2002)). The scores for the three segments were added together to determine the histological scores for individual animals. The results are given in average ±standard error.

As shown in Table 3, the histological score was significantly lower in the group administered KRP-203 than in the placebo group, a demonstration that KRP-203 reduces colitis in IL-10 knockout mice. These results suggest that the test compound KRP-203 is effective in the treatment of inflammatory bowel diseases.

TABLE 3

Histological Score

| Groups tested | Number of Samples | Histological Score |
|---|---|---|
| Placebo group | 8 | 4.1 ± 1.3 |
| KRP-203 group | 8 | 0.3 ± 0.2* |

*$p < 0.05$ vs placebo group (Mann-Whitney's test)

Example 4

Preparation Example

Capsule Preparation (In One Capsule) Composition

| | |
|---|---|
| Compound (KRP-203) | 0.1 mg |
| D-mannitol | 247.5 mg |
| Magnesium stearate | 2.5 mg |

Specifically, the compound of the present invention was mixed with D-mannitol. Magnesium stearate was then blended in the mixture to form a powdery mixture. This mixture was packaged in a capsule to make a capsule preparation.

INDUSTRIAL APPLICABILITY

As set forth, the compound of the present invention proved highly effective in a disease model of inflammatory bowel diseases in humans and caused a significant reduction in the tissue lesion in knockout mice. Thus, the 2-amino-1,3-propanediol derivatives of the present invention and pharmaceutically acceptable salts and hydrates thereof are useful in the treatment or prevention of inflammatory bowel diseases. Accordingly, the present invention provides a therapeutic and prophylactic agent for inflammatory bowel diseases including Crohn's disease, Crohn's disease in large intestine, intestinal Behcet's disease, ulcerative colitis, bleeding rectal ulcer and pouchitis, as well as a method for treating or preventing these diseases.

The invention claimed is:

1. A method for treating an inflammatory bowel disease, which comprises administering to a patient having said disease a therapeutically effective amount of 2-amino-2-[4-(3-benzyloxyphenylthio)-2-chlorophenyl]ethyl-1,3-propanediol or a pharmaceutically acceptable salt thereof.

2. The method for treating an inflammatory bowel disease according to claim 1, wherein the inflammatory bowel disease is Crohn's disease, Crohn's disease in large intestine, intestinal Behcet's disease, ulcerative colitis, bleeding rectal ulcer, or pouchitis.

3. The method for treating an inflammatory bowel disease according to claim 2, wherein the method comprises administering 2-amino-2-[4-(3-benzyloxyphenylthio)-2-chlorophenyl]ethyl-1,3-propanediol hydrochloride.

4. The method for treating an inflammatory bowel disease according to claim 2, wherein the inflammatory bowel disease is inflammatory bowel disease resistant to antimetabolic immunosuppressors, steroids, salazosulfapyridine, or mesalazine.

5. The method for treating an inflammatory bowel disease according to claim 4, wherein the method comprises administering 2-amino-2-[4-(3-benzyloxyphenylthio)-2-chlorophenyl]ethyl-1,3-propanediol hydrochloride.

6. The method for treating an inflammatory bowel disease according to claim 4, wherein the inflammatory bowel disease is Crohn's disease or ulcerative colitis.

7. The method for treating an inflammatory bowel disease according to claim 6, wherein the method comprises administering 2-amino-2-[4-(3-benzyloxyphenylthio)-2-chlorophenyl]ethyl-1,3-propanediol hydrochloride.

8. The method for treating an inflammatory bowel disease according to claim 1, wherein the inflammatory bowel disease is Crohn's disease or ulcerative colitis.

9. The method for treating an inflammatory bowel disease according to claim 8, wherein the method comprises administering 2-amino-2-[4-(3-benzyloxyphenylthio)-2-chlorophenyl]ethyl-1,3-propanediol hydrochloride.

10. The method for treating an inflammatory bowel disease according to claim 1, wherein the method comprises administering 2-amino-2-[4-(3-benzyloxyphenylthio)-2-chlorophenyl]ethyl-1,3-propanediol hydrochloride.

11. A method for treating an inflammatory bowel disease, which comprises administering to a patient having said disease a therapeutically effective amount of 2-amino-2-[4-(3-benzyloxyphenylthio)-2-chlorophenyl]ethyl-1,3-propanediol or a pharmaceutically acceptable salt thereof in combination with at least one other therapeutic agent for an inflammatory bowel disease.

12. The method for treating an inflammatory bowel disease according to claim 11, wherein the at least one other therapeutic agent for an inflammatory bowel disease comprises a sulfasalazine, a steroid, or an immunosuppressor.

13. The method for treating an inflammatory bowel disease according to claim 12, wherein the method comprises administering 2-amino-2-[4-(3-benzyloxyphenylthio)-2-chlorophenyl]ethyl-1,3-propanediol hydrochloride, in combination with the at least one other therapeutic agent for an inflammatory bowel disease.

14. The method for treating an inflammatory bowel disease according to claim 11, wherein the method comprises administering 2-amino-2-[4-(3-benzyloxyphenylthio)-2-chlorophenyl]ethyl-1,3-propanediol hydrochloride, in combination with the at least one other therapeutic agent for an inflammatory bowel disease.

* * * * *